(12) United States Patent
Swedo

(10) Patent No.: US 8,722,936 B2
(45) Date of Patent: May 13, 2014

(54) LOW-VOC POLYAMINES

(75) Inventor: Raymond John Swedo, Mount Prospect, IL (US)

(73) Assignee: ANGUS Chemical Company, Buffalo Grove, IL (US)

(*) Notice: Subject to any disclaimer, the term of this patent is extended or adjusted under 35 U.S.C. 154(b) by 73 days.

(21) Appl. No.: 13/500,168

(22) PCT Filed: Oct. 8, 2010

(86) PCT No.: PCT/US2010/051995
§ 371 (c)(1),
(2), (4) Date: Apr. 4, 2012

(87) PCT Pub. No.: WO2011/044472
PCT Pub. Date: Apr. 14, 2011

(65) Prior Publication Data
US 2012/0196963 A1    Aug. 2, 2012

Related U.S. Application Data

(60) Provisional application No. 61/278,555, filed on Oct. 8, 2009.

(51) Int. Cl.
*C07C 217/42* (2006.01)
*C07C 209/34* (2006.01)

(52) U.S. Cl.
USPC ............................ 564/505; 564/504; 564/495

(58) Field of Classification Search
None
See application file for complete search history.

(56) References Cited

U.S. PATENT DOCUMENTS

| | | | |
|---|---|---|---|
| 4,992,586 A | 2/1991 | Junino et al. | |
| 5,227,528 A | 7/1993 | Webster et al. | |
| 5,284,644 A | 2/1994 | Kruper, Jr. et al. | |
| 5,461,176 A | 10/1995 | Sun et al. | |
| 2003/0023088 A1 | 1/2003 | Morris et al. | |

FOREIGN PATENT DOCUMENTS

| | | | | |
|---|---|---|---|---|
| BE | 629098 A | 9/1963 | | |
| CN | 1093377 A | 10/1994 | | |
| EP | 0163214 A2 | 12/1985 | | |
| EP | 290883 | 11/1988 | | |
| EP | 0 363 877 A1 | * 4/1990 | ............ | C08G 65/32 |
| EP | 0373671 A2 | 6/1990 | | |
| EP | 391733 | 10/1990 | | |
| EP | 394016 | 10/1990 | | |
| EP | 451539 | 10/1991 | | |

OTHER PUBLICATIONS

Database CAPLUS in STN, Acc. No. 1969:53505, Phillip, Australian Journal of Chemistry (1968), 21(11), p. 2797-2800 (abstract).*
Database CAPLUS in STN, Acc. No. 1965:489817, Andres et al., DE 1199987 (Sep. 2, 1965) (abstract).*
T. Tsui, T. Udea; Synthesis of 2-Guanidino-2-methylpropylamine Derivatives; Chemical and Pharmaceutical Bulletin; vol. 12, 1964, pp. 946-950, XP002610454.
Stanislav Kafka, Antonin Klasek, Petr Sedmera; N-(2-Methyl-2-nitropropyl) and N-Nitroso Derivatives of Some Diamines; Collection of Czechoslovak Chemical Communications; vol. 60, 1995, pp. 1541-1550, XP002610455.
Agnieszka Szczepanska, et al; A New Approach to the Synthesis of Chiral Tetaazacoronands Derived from L-Alanine; Heterocycles, Elsevier Science Publishers B.V. Amsterdam, NL.; vol. 52, No. 2, Feb. 1, 2000, pp. 537-540, XP008129342.
Gerhard Greiner, Ingrid Maier; Anthrylmethylamines and Anthrylmethylazamacrocycles as fluorescent pH sensors—a systematic study of their static and dynamic properties; Journal of the Chemical Society—Perkin Transactions 2, 2002, p. 1005-1011, XP002610456.
Min-Hoi Choi, Jo Kim, et al; Inter-and intra-molecular pathways in polyamine synthesis from diamines; Journal of the Chemical Society—Dalton Transactions, 2001, p. 707-722, XP002610457.
Swarna A Gamage, Julie A. Spicer, et al; Dicationic Bis (9-methylphenazine-1-carboxamides): Relationships between Biological Activity and Linker Chain Structure for a Series of Potent Topoisomerase Targeted Anticancer Drugs; Journal of Medicinal Chemistry, vol. 44, No. 9, 2001, pp. 1407-1415, XP002610458.
Vivienne A. White, Nicholas J. Long, Neil Robertson; Synthesis of nitrogen and sulfur macrocycles with cis exogenous oxygen and sulfur donor atoms; Organic & Biomolecular Chemistry, vol. 3, 2005, pp. 4268-4273, XP002610460.
Yi Li, Manfred Hesse; The Synthesis of cyclic Spermidine Alkaloids: Analogues of Buchnerine and Budmunchiamine C; Helvetica Chimica Acta; vol. 86, 2003, pp. 310-323, XP002610461.
M. E. Hultquist, E. H. Northey; Reaction of bis-beta-Chloroethyl Ether with Ethylenediamine; Journal of the American Chemical Society, vol. 62, 1940, pp. 447-448, XP002610462.

* cited by examiner

*Primary Examiner* — Brian J Davis
(74) *Attorney, Agent, or Firm* — Kenneth Crimaldi

(57) ABSTRACT

A compound having formula (I)

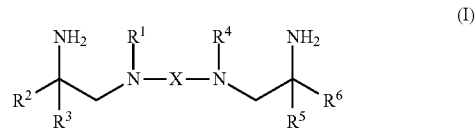

wherein $R^1$, $R^2$, $R^3$, $R^4$, $R^5$ and $R^6$ independently are hydrogen, $C_1$-$C_{10}$ alkyl, $C_5$-$C_{10}$ cycloalkyl, $C_6$-$C_{10}$ aryl or $C_7$-$C_{20}$ aralkyl; X is a difunctional group selected from the group consisting of $C_2$-$C_{20}$ alkyl, $C_5$-$C_{20}$ cycloalkyl, $C_6$-$C_{10}$ aryl, $C_8$-$C_{20}$ aryl alkyl, $C_4$-$C_{20}$ heteroalkyl or $C_{10}$-$C_{20}$ aryl heteroalkyl.

6 Claims, No Drawings

LOW-VOC POLYAMINES

BACKGROUND

This invention relates generally to a polyamine compound useful in coating compositions and other applications for pH adjustment and as a dispersing agent.

AMP (2-amino-2-methylpropanol) is used for pH adjustment of coating compositions and other formulations requiring pH adjustment and a dispersing agent. Compounds useful for this purpose, but having lower volatility, as measured by standard VOC (volatile organic compound) tests would be desirable. EP 391,733 discloses a compound having the formula

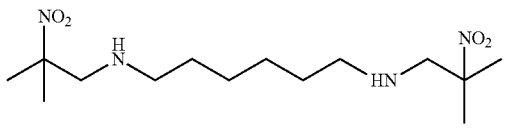

but this reference does not disclose or suggest a polyamine compound as claimed in the present application.

The problem addressed by this invention is to find polyamine compounds useful in coating compositions and other applications for pH adjustment and as dispersing agents.

STATEMENT OF INVENTION

The present invention is directed to a compound having formula (I)

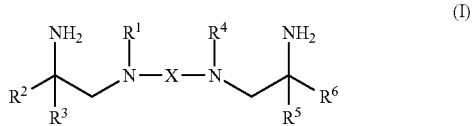

wherein $R^1$, $R^2$, $R^3$, $R^4$, $R^5$ and $R^6$ independently are hydrogen, $C_1$-$C_{10}$ alkyl, $C_5$-$C_{10}$ cycloalkyl, $C_6$-$C_{10}$ aryl or $C_7$-$C_{20}$ aralkyl; X is a difunctional group selected from the group consisting of $C_2$-$C_{20}$ alkyl, $C_5$-$C_{20}$ cycloalkyl, $C_6$-$C_{10}$ aryl, $C_8$-$C_{20}$ aryl alkyl, $C_4$-$C_{20}$ heteroalkyl or $C_{10}$-$C_{20}$ aryl heteroalkyl.

The present invention is further directed to a method for adjusting pH in a coating composition; said method comprising adding to a coating composition having a pH below 7 a sufficient amount of a compound of formula (I) to produce a final pH from 7.5 to 9.5 wherein $R^1$, $R^2$, $R^3$, $R^4$, $R^5$ and $R^6$ independently are hydrogen, $C_1$-$C_{10}$ alkyl, $C_5$-$C_{10}$ cycloalkyl, $C_6$-$C_{10}$ aryl or $C_7$-$C_{20}$ aralkyl; X is a difunctional group selected from the group consisting of $C_2$-$C_{20}$ alkyl, $C_5$-$C_{20}$ cycloalkyl, $C_6$-$C_{10}$ aryl, $C_8$-$C_{20}$ aryl alkyl, $C_4$-$C_{20}$ heteroalkyl or $C_{10}$-$C_{20}$ aryl heteroalkyl.

The present invention is further directed to a method for producing a compound of formula (I) wherein $R^1$, $R^2$, $R^3$, $R^4$, $R^5$ and $R^6$ independently are hydrogen, $C_1$-$C_{10}$ alkyl, $C_5$-$C_{10}$ cycloalkyl, $C_6$-$C_{10}$ aryl or $C_7$-$C_{20}$ aralkyl; X is a difunctional group selected from the group consisting of $C_2$-$C_{20}$ alkyl, $C_5$-$C_{20}$ cycloalkyl, $C_6$-$C_{10}$ aryl, $C_8$-$C_{20}$ aryl alkyl, $C_4$-$C_{20}$ heteroalkyl or $C_{10}$-$C_{20}$ aryl heteroalkyl. The method comprises reducing a compound of formula (II)

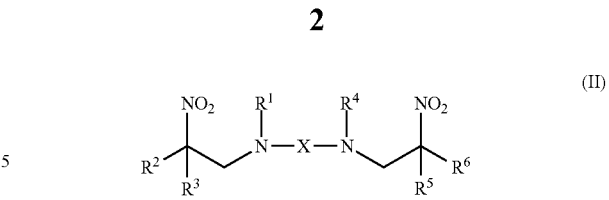

by contacting the compound of formula (II) with a reducing agent capable of reducing aliphatic nitro groups.

DETAILED DESCRIPTION

All percentages are weight percentages ("wt %"), unless otherwise indicated. Concentrations in parts per million ("ppm") are calculated on a weight/volume basis. An "aqueous" composition is one comprising at least 30 wt % water, alternatively at least 35 wt % water, alternatively at least 38 wt % water. Preferably, aqueous compositions comprise no more than 5 wt % organic solvent. An "alkyl" group is a hydrocarbyl group having from one to twenty carbon atoms, unless otherwise specified, in a linear or branched arrangement. Alkyl groups optionally have one or more double or triple bonds. Substitution on alkyl groups of one or more hydroxy or alkoxy groups is permitted. Preferably, alkyl groups are saturated and unsubstituted. A "cycloalkyl" group is an alkyl group containing at least one saturated ring. A "heteroalkyl" group is an alkyl group in which at least one carbon has been replaced by O, NR, or S, wherein R is hydrogen, alkyl, aryl or aralkyl; e.g., —$CH_2CHR'(OCH_2CHR')_n$— where R' is hydrogen, methyl or ethyl and n is from one to nine, or an upper limit determined by the maximum size of the heteroalkyl group and the identity of R'. The carbon number of a heteroalkyl group is the actual number of carbon atoms in the heteroalkyl group, and does not include incorporated heteroatoms. In some embodiments of the invention, a heteroalkyl group has only oxygen heteroatoms and the ratio of carbon atoms to oxygen atoms is from 5:1 to 2:1, alternatively from 4:1 to 2.5:1. In some embodiments of the invention, a heteroalkyl group is attached through carbon atoms at either end of the chain. An "aryl" group is a substituent derived from an aromatic hydrocarbon compound. An aryl group has a total of from six to twenty ring atoms, unless otherwise specified, and has one or more rings which are separate or fused. An "aralkyl" group is an "alkyl" group substituted by an "aryl" group. An "aryl alkyl" group is a difunctional group in which a difunctional aryl group is inserted into an alkyl group, e.g., —$(CH_2)_xC_6H_4(CH_2)_y$—, where $C_6H_4$ is o-, m- or p-phenylene and x and y may be the same or different, preferably the same, and have values consistent with the overall size of the aryl alkyl group and the identity of the inserted aryl group. An "aryl heteroalkyl" group is a difunctional group in which a difunctional aryl group is inserted into a heteroalkyl group. Substitution on aryl groups of one or more of the following groups: halo, cyano, nitro, hydroxy, alkoxy, alkyl, heteroalkyl, alkanoyl, amino, or amino substituted by one or more of alkyl, aryl, aralkyl, heteroalkyl or alkanoyl is permitted, with substitution by one or more halo groups being possible on alkyl, heteroalkyl, alkanoyl or alkoxy groups. Preferably, aryl groups do not contain halogen atoms. In one preferred embodiment of the invention, aryl groups are unsubstituted or substituted only by alkyl groups. A difunctional group is a substituent group having two points of attachment, e.g., one example of a difunctional alkyl group would be —$(CH_2)_x$—, where x could be from two to twenty.

In some embodiments of the invention, $R^1$ and $R^4$ independently are hydrogen or $C_1$-$C_6$ alkyl; alternatively hydrogen or $C_1$-$C_4$ alkyl; alternatively hydrogen, methyl or ethyl; alternatively hydrogen or methyl; alternatively hydrogen. In some embodiments of the invention, $R^1$ and $R^4$ are the same. In some embodiments of the invention, $R^2$, $R^3$, $R^5$ and $R^6$ independently are hydrogen, $C_1$-$C_6$ alkyl, $C_5$-$C_7$ cycloalkyl, $C_6$-$C_{10}$ aryl or $C_7$-$C_{10}$ aralkyl; alternatively hydrogen or $C_1$-$C_6$ alkyl; alternatively hydrogen or $C_1$-$C_4$ alkyl; alternatively $C_1$-$C_4$ alkyl; alternatively hydrogen, methyl or ethyl; alternatively methyl or ethyl; alternatively methyl. In some embodiments of the invention, $R^3$ is the same as $R^5$ and $R^2$ is the same as $R^6$. In some embodiments of the invention, $R^2$, $R^3$, $R^5$ and $R^6$ are the same.

In some embodiments of the invention, X is a difunctional group selected from the group consisting of $C_2$-$C_{10}$ alkyl, $C_5$-$C_{10}$ cycloalkyl, $C_6$-$C_8$ aryl, $C_8$-$C_{12}$ aryl alkyl, $C_4$-$C_{20}$ heteroalkyl and $C_{10}$-$C_{20}$ aryl heteroalkyl; alternatively $C_2$-$C_{10}$ alkyl, $C_4$-$C_{20}$ heteroalkyl and $C_{10}$-$C_{20}$ aryl heteroalkyl; alternatively $C_3$-$C_8$ alkyl and $C_6$-$C_{15}$ heteroalkyl; alternatively $C_6$-$C_{15}$ heteroalkyl. In some embodiments of the invention, X is symmetric, i.e., there is a plane of symmetry perpendicular to the length of X.

In some embodiments of the invention, the compound of formula (I) is prepared by combining a nitro alcohol of formula (III) with a compound having two terminal primary or secondary amino groups, as in formula (IV), as shown below

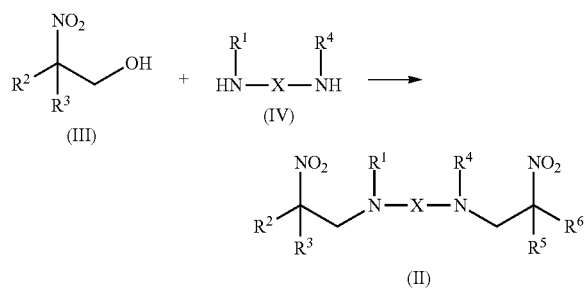

to produce a nitro compound of formula (II), followed by reduction of nitro compound (II) to the compound of formula (I). Reduction of compound (II) may be accomplished using any reagent capable of reducing aliphatic nitro groups. Examples of such reducing agents include hydrogen gas in combination with a catalyst, for example, Raney nickel, supported palladium or supported platinum; or with formic acid and palladium in the absence of hydrogen; and other reducing agents including lithium aluminum hydride, sodium or lithium and liquid ammonia, zinc, tin, or iron with hydrochloric acid, aluminum hydride/aluminum chloride, sodium hydrosulfide, or ammonium sulfide. Preferred reducing agents include hydrogen gas in combination with any of the following catalysts: Raney nickel, palladium on carbon, or platinum on carbon. Conditions for hydrogenation of nitro groups are well known, e.g., 25-70° C. at 103-3800 KPa.

In some embodiments of the invention, compound (IV) has polymerized residues, e.g., two-six residues, of alkylene oxides, e.g., ethylene oxide, propylene oxide and butylene oxide, capped with aminoalkyl groups, e.g., $C_2$-$C_4$ aminoalkyl groups. In some embodiments of the invention, X represents a mixture of groups having the average formula —$CH(CH_3)CH_2(OCH_2CH(CH_3))_n$—, where n is about 2.7. This mixture contains at least the species having n equal to 2, 3 and 4, which correspond to X being a $C_9$, $C_{12}$ or $C_{15}$ heteroalkyl group, respectively. In some embodiments of the invention, X is a $C_6$-$C_9$ heteroalkyl group having two oxygen atoms.

When the compound of formula (I) is used to adjust pH in an aqueous coating composition or other aqueous composition having an initial pH less than 7, the amount of compound (I) added clearly can vary depending on the initial pH, desired final pH, and other components present in the composition. However, one skilled in the art can easily determine the necessary amount of compound (I). In acrylic latex coating compositions, typically the amount of compound (I) would be in the range from 10 wt % to 125 wt % of total weight of carboxylic acid groups in the coating composition, alternatively from 25 wt % to 100 wt %. In some embodiments of the invention, the initial pH of the aqueous composition is from 2-7, alternatively from 2.5-6. The target pH value preferably is from 7.8 to 9.3, alternatively from 8 to 9.2. In some embodiments of the invention, the aqueous coating composition is an acrylic latex comprising copolymers of acrylic or methacrylic acid with $C_1$-$C_8$ alkyl acrylates or methacrylates. In some embodiments of the invention, the acrylic latex comprises 40-65 wt % polymer solids, alternatively 45-62 wt %, alternatively 45-55 wt %. The compound of formula (I) has the added benefit of being a dispersing agent for pigment and other components of the typical coating composition or other compositions.

EXAMPLES

Synthesis of N,N'-(3,3'-(2,2'-oxybis(ethane-2,1-diyl)bis(oxy))bis(propane-3,1-diyl))bis(2-methyl-2-nitropropan-1-amine (TTDA-bis-NMP)

A 1-L 3-neck flask was equipped with a magnetic stirrer, a reflux condenser with nitrogen blanket, and a thermocouple. The flask was charged with 119.14 grams (1.0 mole) of NMP and with 110.16 grams (0.5 moles) of 4,7,10-trioxa-1,13-tridecanediamine (TTDA). The clear, colorless solution was stirred under nitrogen at room temperature for 11 days. Hexanes (ca. 100 mL) were added to the reaction mixture, and it was heated to reflux with the removal of water as the azeotrope. The hexanes were then removed by vacuum distillation. The yield of TTDA-bis-NMP as a clear yellow liquid was 209 grams (99%). GC analysis showed the presence of small amounts of ca. 11% of residual NMP. GC/MS, IR, $^1$H- and $^{13}$C-NMR analyses were consistent with the proposed structure.

Synthesis of $N^1$,$N^{1'}$-(3,3'-(2,2'-oxybis(ethane-2,1-diyl)bis(oxy))bis(propane-3,1-diyl))bis(2-methylpropane-1,2-diamine (TTDA-bis-AMP)

A 2-L 316 stainless steel PARR reactor was charged with 209 grams (0.495 moles) of TTDA-bis-NMP, 500 grams of methanol, and 36.7 grams of water wet RaNi 3111 catalyst. The reactor was flushed with nitrogen, then pressurized with hydrogen. The reduction was conducted at 550 psig hydrogen (3790 KPa) at 65° C. The reduction was complete in about 1.5 hours. The reactor mixture was filtered to remove the catalyst; the filtrate was clear and pale blue in color. The methanol and water were removed from the filtrate by rotary evaporation to give 169 grams (94%) of TTDA-bis-AMP as a clear, blue liquid. GC analysis showed the presence of 8.4% of the mono-adduct (TTDA-AMP). GC/MS, IR, $^1$H- and $^{13}$C-NMR analyses were consistent with the proposed structure. Titration gave $pK_1$=9.77 and $pK_2$=6.45. Volatility by the modified EPA Test Method 24 was 0.2%.

Synthesis of JEFFAMINE D230-bis-NMP (JD230-bis-NMP)

A 1-L 3-neck flask was equipped with a mechanical stirrer, a reflux condenser with nitrogen blanket, and a heating mantle with a temperature controller and a thermocouple. The flask was charged with 238.3 grams (2.0 moles) of NMP and with 230.4 grams (1.0 mole) of JEFFAMINE D230. The mixture was stirred under nitrogen at room temperature to give a clear, colorless solution. The solution was stirred at room temperature for 24 days, then 150 mL of hexanes were added and the mixture was heated to reflux with removal of water as the azeotrope. The hexanes were then removed by vacuum distillation. The yield of JD230-bis-NMP as a clear yellow liquid was 432.3 grams (100%). IR, $^1$H- and $^{13}$C-NMR analyses were consistent with the proposed structure.

Synthesis of JEFFAMINE D230-bis-AMP (JD230-bis-AMP)

A 2-L 316 stainless steel PARR reactor was charged with 400 grams (0.93 moles) of JD230-bis-NMP, 400 mL of methanol, and 52.1 grams of water wet RaNi 3111 catalyst. The reactor was flushed with nitrogen, then pressurized with hydrogen. The reduction was conducted at 490 psig hydrogen (3380 KPa) at 65° C. The reduction was complete in about 2 hours. The reactor mixture was filtered to remove the catalyst; the filtrate was clear and pale yellow. The methanol and water were removed from the filtrate by rotary evaporation to give 330.3 grams (96%) of JD230-bis-AMP as a clear, light yellow liquid. IR, $^1$H- and $^{13}$C-NMR analyses were consistent with the proposed structure. Titration gave $pK_1$=9.6 and $pK_2$=5.9. Volatility by the modified EPA Test Method 24 was 2%.

Synthesis of N,N'-(2,2'-ethane-1,2-diylbis(oxy))bis(ethane-2,1-diyl)bis(2-methyl-2-nitropropan-1-amine) (EDBDA-bis-NMP)

A 500 mL 3-neck flask was equipped with a magnetic stirrer, a reflux condenser with nitrogen blanket, and a heating mantle with a temperature controller and a thermocouple.

The flask was charged with 165.57 grams (1.39 moles) of NMP, and with 103.0 grams (0.695 moles) of 2,2'-(ethylenedioxy)bis(ethylamine) (EDBDA). The mixture was stirred under nitrogen at room temperature to give a clear, colorless solution. After stirring at room temperature for 5 days, the reaction mixture was heated to 60° C. After 7 hours at 60° C., LC analysis showed no remaining NMP. Hexanes (100 mL) were added and the mixture was heated to reflux with removal of water as the azeotrope. The hexanes were then removed by vacuum distillation. The yield of EDBDA-bis-NMP as a clear yellow liquid was 243.5 grams (98%). LC/MS, IR, $^1$H- and $^{13}$C-NMR analyses were consistent with the proposed structure. LC/MS also detected the presence of some tris-adduct in which EDBDA-bis-NMP reacted with an additional NMP.

Synthesis of $N^1,N^{1'}$-(2,2'-(ethane-1,2-diylbis(oxy))bis(ethane-2,1-diyl)bis(2-methylpropane-1,2-diamine) (EDBDA-bis-AMP)

A 2-L 316 stainless steel PARR reactor was charged with 237.2 grams (0.68 moles) of EDBDA-bis-NMP, 400 mL of methanol, and 33.3 grams of water wet RaNi 3111 catalyst. The reactor was flushed with nitrogen, then pressurized with hydrogen. The reduction was conducted at 490 psig (3380 KPa) hydrogen at 65° C. The reduction was complete in about 1.5 hours. The reactor mixture was filtered to remove the catalyst; the filtrate was clear and colorless. The methanol and water were removed from the filtrate by rotary evaporation to give 192.3 grams (98%) of EDBDA-bis-AMP as a clear, nearly colorless liquid. IR, $^1$H- and $^{13}$C-NMR analyses were consistent with the proposed structure. GC/MS also detected the presence of 4.8% of the mono-adduct EDBDA-AMP, 1% of monomethyl EDBDA-bis-AMP, 1.2% of the monoimidazolidine derivative of EDBDA-bis-AMP, and 1.6% of tris-adduct in which EDBDA-bis-NMP reacted with an additional NMP. Titration gave $pK_1$=9.7 and $pK_2$=5.8. Volatility by the modified EPA Test Method 24 was 0%.

Synthesis of $N^1,N^6$-bis(2-methyl-2-nitropropyl)hexane-1,6-diamine [114136-87-7] (HD-bis-NMP)

A 500 mL 3-neck flask was equipped with a magnetic stirrer, a reflux condenser with nitrogen blanket, and a heating mantle with a temperature controller and a thermocouple. The flask was charged with 119.14 grams (1.0 mole) of NMP, with 58.18 grams (0.5 moles) of 1,6-hexanediamine, with 10 grams of water, and with 50 mL of methanol. The mixture was stirred under nitrogen at room temperature to give a clear yellow solution. After stirring at room temperature for 5 days, the methanol was removed by distillation, then ca. 100 mL of hexanes were added. The mixture was heated to reflux with the removal of water as the azeotrope. The hexanes were then removed by vacuum distillation. The yield of HD-bis-NMP as a clear yellow oil was 151.9 grams (95%). LC/MS, IR, $^1$H- and $^{13}$C-NMR analyses were consistent with the proposed structure. LC/MS analysis also showed the presence of some tris-adduct in which HD-bis-NMP reacted with an additional NMP.

Synthesis of $N^1,N^{1'}$-(hexane-1,6-diyl)bis(2-methylpropane-1,2-diamine) (HD-bis-AMP)

A 2-L 316 stainless steel PARR reactor was charged with 141 grams (0.44 moles) of EDBDA-bis-NMP, 500 mL of methanol, and 25.8 grams of water wet RaNi 3111 catalyst. The reactor was flushed with nitrogen, then pressurized with hydrogen. The reduction was conducted at 490 psig hydrogen (3380 KPa) at 65° C. The reduction was complete in about 1 hour. The reactor mixture was filtered to remove the catalyst; the filtrate was clear and pale yellow. The methanol and water were removed from the filtrate by rotary evaporation to give 110.9 grams (97%) of HD-bis-AMP as a clear, pale yellow liquid. The liquid solidified on standing to give a white crystalline solid having MP=25-35° C. GC/MS, IR, $^1$H- and $^{13}$C-NMR analyses were consistent with the proposed structure. GC/MS also showed the presence of some mono-adduct HD-AMP and some HD-bis-AMP mono-imidazolidine. Titration gave $pK_1$=10.0 and $pK_2$=6.9. Volatility by the modified EPA Test Method 24 was 8.9%.

The Evaluation of TA-AMP and TA-ACyHM as Neutralizing Agent and Co-dispersants in Semi-gloss Latex Paint The performance of JD230-bis-AMP, EDBDA-bis-AMP, TTDA-bis-AMP, and HD-bis-AMP were evaluated against AMP in semi-gloss latex paint formulations. The novel polyamino alcohols replaced AMP on an equimolar basis. ANGUS AEPD VOX 1000 and Vantex T are commercial low odor, low VOC amines and were similarly used to replace AMP on an equimolar basis. The baseline AMP formulation was as described below in the table. The first three "Grind" ingredients were combined in the indicated order and agitated 10 minutes at high speed, then the remaining Grind ingredients were added at low speed. The complete Grind was dispersed at high speed for 15 minutes, and then the "Letdown" ingredients, except for the last charge of DREWPLUS Y-381 defoamer, were added and dispersed at high speed for 10 minutes. The last charge of defoamer was added and the complete mixture agitated at low speed for 10 minutes. The pH of the formula was >9 and its viscosity was 86-92 KU.

|  | spec. grav. | weight |
|---|---|---|
| GRIND | | |
| Water | 1.00 | 140.00 |
| CELLOSIZE QP300[1] | 1.41 | 5.00 |
| water | 1.00 | 10.00 |
| TAMOL 1124[2] | 1.19 | 5.00 |
| TRITON CF-10[3] | 1.08 | 2.00 |
| TRITON GR-PG70[4] | 1.11 | 0.43 |
| DREWPLUS Y-381 defoamer | 0.87 | 1.00 |
| ethylene glycol | 1.12 | 30.00 |
| amine | 0.94 | 2.00 |
| OMYACARB UF calcium carbonate | 2.72 | 25.00 |
| water | 1.00 | 20.00 |
| LETDOWN | | |
| UCAR LATEX 379, vinyl acrylic binder | 1.09 | 375.00 |
| UCAR LATEX 6030, acrylic binder | 1.06 | 47.00 |
| butyl carbitol | 0.95 | 6.00 |
| ARCHER RC reactive coalescent[5] | 0.92 | 12.00 |
| DREWPLUS Y-381 defoamer | 0.87 | 1.50 |
| TIPURE R942 $TiO_2$ slurry (76.5% solids) | 2.33 | 250.00 |
| ACRYSOL RM-5000 rheology modifier[6] | 1.04 | 30.00 |
| water | 1.00 | 64.58 |
| DREWPLUS Y-381 defoamer | 0.87 | 1.50 |
| Total | | 1028.00 |

[1]HEC thickener, modified cellulose, available from DOW
[2]Dispersant, acrylic copolymer, available from ROHM and HAAS
[3]Benzyl-polyethylene glycol-t-octylphenyl ether
[4]Anionic sulfosuccinate surfactant
[5]Fatty acid ester alcohol
[6]Non-ionic urethane polymer, available from ROHM and HAAS Samples of the formulation made with various amines was tested, with the results presented in the following tables. The pH of each formulation is measured with a Corning Model 430 pH meter with a ceramic-junction probe. Krebs-units (KU) viscosity is measured with a Stormer viscometer with a stroboscopic timer (ASTM D562). Sample temperatures are 24±1° C., except for the initial values, due to the warming during mixing. The high shear ("ICI") viscosity is measured according to ASTM D 4287 using a Brookfield CAP 1000+ viscometer at a shear rate of 12,000 s$^{-1}$ at 900 rpm, with a 0.45° cone of radius 1.511 cm, and a sample temperature controlled at 25° C.

Color and gloss measurements are done on films applied with a 3-mil wet-film drawdown bar to Leneta Form 3-B opacity charts. Additional drawdowns are made from the heat-aged stability samples after 2 weeks at 60° C. Panels are dried at least 24 hours at room temperature before measurement.

Color measurements are done with a BYK-Gardner Color Guide Sphere color meter (D65 source/10° observer), which measures reflectance spectra in conformity to ASTM E 1164. The meter calculates color parameters according to the CIE L*a*b* color system. Yellowness is reported here in terms of the b* (yellow-blue scale) parameter. Gloss at 60° is measured with a BYK-Gardner micro-TRI-gloss meter in accordance with ASTM D 523.

Wet-scrub resistance is measured with a Gardco-Model D10 washability, wear, and friction tester, with a fixed speed of 37 cycles/minute according to ASTM D 2486. Replicate side-by-side drawdowns are drawn on Leneta P-121-10N black plastic panels with the 7-mil (180 μm) gap side of a Dow latex bar. The panels are dried 7 days at 50% relative humidity at 25° C. The panels are secured to the stage of the scrub tester with shims under each of the side-by-side films to give a raised test area. Before each 400 cycles of the test, 10 g of the specified abrasive medium and 5 mL of water are placed in the path of the scrub brush. The end point for each paint film is recorded when the brush wears a continuous line of complete paint removal across the width of the raised test surface.

Blocking is measured according to ASTM D 4946 at room temperature and at 50° C. Films of 3-mil (76 μm) wet-film thickness applied to opacity charts are dried for 3 and 7 days at 50% relative humidity at 25° C. before testing. For each test, coated panels are cut into triplicate pairs of 1½ inch (3.8 cm) squares. Each pair of squares is placed face to face, then each pair is covered with a No. 8 rubber stopper. A 1 kg weight is placed on the rubber stopper. The room temperature tests are conducted for 1 hour, and the 50° C. oven tests are conducted for 30 minutes. At the end of each time period, the weights are removed and the pairs of squares are peeled apart with slow, steady force. The amount of adhesion is observed and evaluated on a scale of 0 (greatest adhesion) to 10 (least adhesion).

Amine pK values are determined by titration; amine VOC values are determined via EPA method 24.

| amine | formulation particle size, μm | formulation pH | % VOC amine |
|---|---|---|---|
| 2-amino-2-methylpropanol (AMP) | 0.617 | 9.3 | 100 |
| JD230-bis-AMP | 0.600 | 9.5 | 2.0 |
| HD-bis-AMP | 0.626 | 9.7 | 8.9 |
| EDBDA-bis-AMP | 0.591 | 9.7 | 0.0 |
| TTDA-bis-AMP | 0.615 | 9.6 | 0.2 |
| VOX 1000[1] | 0.620 | 9.0 | 27.0 |
| VANTEX T[2] | 0.621 | 9.0 | 21.0 |

[1]2-amino-2-ethyl-1,3-propanediol
[2]N-butyl-N,N-diethanolamine

Entries between the double lines are amines within the scope of the present invention and the others are comparative. A smaller formulation particle size indicates better dispersion of pigment in the formulation.

| amine | film opacity | film gloss (60°) | film color[1] | film yellowing[2] |
|---|---|---|---|---|
| AMP | 96.520 | 28.5 | 0.75 | 1.4 |
| JD230-bis-AMP | 97.550 | 27.0 | 1.21 | |
| HD-bis-AMP | 95.500 | 27.0 | 1.21 | 2.7 |
| EDBDA-bis-AMP | 96.250 | 27.0 | 1.10 | 2.5 |
| TTDA-bis-AMP | 97.500 | 20.0 | 1.00 | |
| VOX 1000 | 97.575 | 31.0 | 0.85 | 1.7 |
| VANTEX T | 97.100 | 30.0 | 0.82 | 1.7 |

[1]b* white
[2]QUVB 116 hours

The invention claimed is:
1. A compound having formula (I)

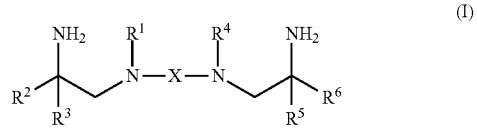

wherein $R^1$, $R^2$, $R^3$, $R^4$, $R^5$ and $R^6$ independently are hydrogen, $C_1$-$C_{10}$ alkyl, $C_5$-$C_{10}$ cycloalkyl, $C_6$-$C_{10}$ aryl or $C_7$-$C_{20}$ aralkyl; X is a difunctional $C_9$-$C_{15}$ heteroalkyl group having only oxygen heteroatoms.

2. The compound of claim 1 in which $R^1$ and $R^4$ independently are hydrogen or $C_1$-$C_6$ alkyl.

3. The compound of claim 2 in which $R^2$, $R^3$, $R^5$ and $R^6$ independently are hydrogen or $C_1$-$C_6$ alkyl.

4. The compound of claim 3 in which $R^1$ and $R^4$ both are hydrogen or methyl and $R^2$, $R^3$, $R^5$ and $R^6$ independently are hydrogen or $C_1$-$C_4$ alkyl.

5. A method for producing a compound of formula (I)

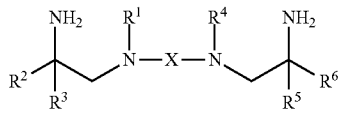

(I)

wherein $R^1$, $R^2$, $R^3$, $R^4$, $R^5$ and $R^6$ independently are hydrogen, $C_1$-$C_{10}$ alkyl, $C_5$-$C_{10}$ cycloalkyl, $C_6$-$C_{10}$ aryl or $C_7$-$C_{20}$ aralkyl; X is a difunctional $C_9$-$C_{15}$ heteroalkyl group having only oxygen heteroatoms;

said method comprising reducing a compound of formula (II)

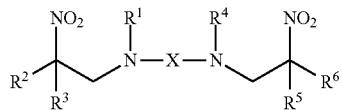

(II)

by contacting the compound of formula (II) with a reducing agent capable of reducing aliphatic nitro groups.

6. The compound of claim 4 in which $R^1$ and $R^4$ are hydrogen; and $R^2$, $R^3$, $R^5$ and $R^6$ are methyl.

* * * * *